United States Patent [19]
Hamilton

[11] Patent Number: 5,520,167
[45] Date of Patent: May 28, 1996

[54] NEBULIZER MASK ADAPTOR RING

[75] Inventor: Lyle H. Hamilton, Wauwatosa, Wis.

[73] Assignee: The Brewer Company, Menomonee Falls, Wis.

[21] Appl. No.: 114,562

[22] Filed: Aug. 31, 1993

[51] Int. Cl.⁶ .................................................. A61M 39/10
[52] U.S. Cl. ................. 128/200.23; 128/200.24; 128/206.21; 128/912; 285/334.1
[58] Field of Search ................ 128/200.24, 202.27, 128/206.21, 200.23, 912; 285/342.1, 342.2, 342.3, 12

[56] References Cited

U.S. PATENT DOCUMENTS

| | | | |
|---|---|---|---|
| 3,388,705 | 6/1968 | Grosshandler | 128/912 X |
| 3,602,531 | 8/1971 | Patry | 285/177 |
| 4,506,665 | 3/1985 | Andrews et al. | 128/202.27 |
| 4,580,556 | 4/1986 | Kondur | 128/206.28 |
| 4,582,054 | 4/1986 | Ferrer | 128/200.23 |
| 4,827,921 | 5/1989 | Rugheimer | 128/202.27 |
| 4,852,563 | 8/1989 | Gross | 128/202.27 |
| 4,919,127 | 4/1990 | Pell | 128/207.14 |
| 4,938,210 | 7/1990 | Shene | 128/203.12 |
| 4,953,547 | 9/1990 | Poole, Jr. | 128/203.12 |
| 5,012,804 | 5/1991 | Foley et al. | 128/200.23 |
| 5,062,423 | 11/1991 | Matson et al. | 128/207.15 |
| 5,137,520 | 8/1992 | Maxson et al. | 128/DIG. 26 |

FOREIGN PATENT DOCUMENTS

| | | | |
|---|---|---|---|
| 1294835 | 4/1962 | France | 128/200.23 |
| 4028387 | 3/1992 | Germany | 128/200.23 |
| 2230456 | 10/1990 | United Kingdom | 128/200.21 |
| 9311817 | 7/1993 | WIPO | 128/200.23 |

OTHER PUBLICATIONS

Monaghan Medical Corp Brochure, "Topical Dosage for Young Asthmatic Children with M.D.I. Aerosol Medications", Apr. 1989.

Primary Examiner—Ren Yan
Assistant Examiner—William J. Deane, Jr.
Attorney, Agent, or Firm—Wheeler & Kromholz

[57] ABSTRACT

A mask adaptor ring for connecting a medication inhaler having an extended cylindrical breathing tube to masks with attachment connections of child and adult size, the mask adaptor comprising a compound annular ring with a central opening, the central opening having an inlet end and an outlet end, the inlet end having an inside diameter slightly larger than the outer diameter of a child mask attachment, the outside diameter of the outlet end having a diameter slightly smaller than inner diameter of the adult mask attachment, and the inlet end having an outside diameter slightly smaller than the outlet end opening of the extended breathing tube. A skirting is provided for size adaptability to outlet end openings of various cylindrical breathing tubes. The invention also has a center flange disposed between its inlet end and its outlet end, the flange having a diameter larger than the outer diameter of the adult mask attachment and of the outlet end opening of the extended breathing tube. The inlet end and the outlet end of the mask adaptor ring are tapered so that they are at their smallest at the top and bottom of the mask adaptor ting. The taper is at an angle of 1°–4° and tapers outward from the top and bottom toward the center flange. The central opening at the outlet end is tapered inward at an angle of 1°–4° toward the center flange. The tapers allow for slight variations in mask attachment and extended cylindrical tube sizes.

1 Claim, 2 Drawing Sheets

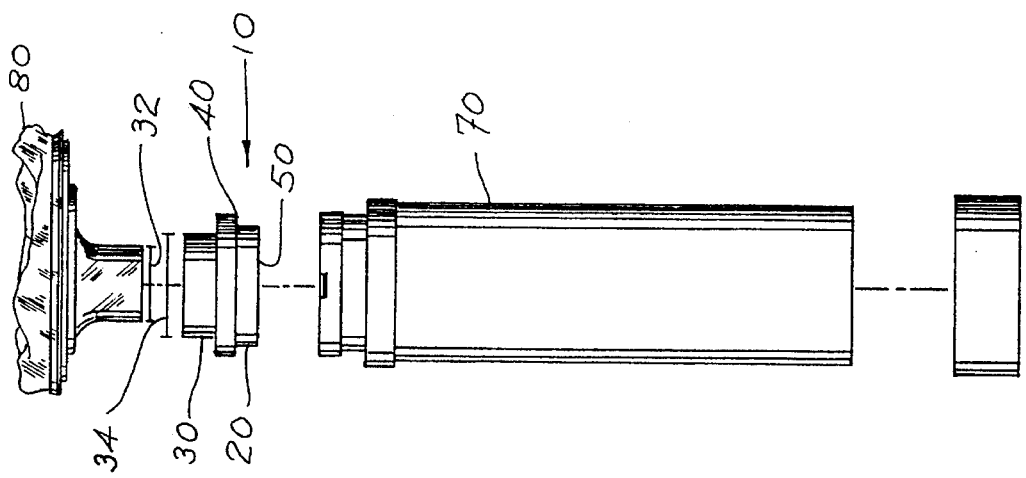
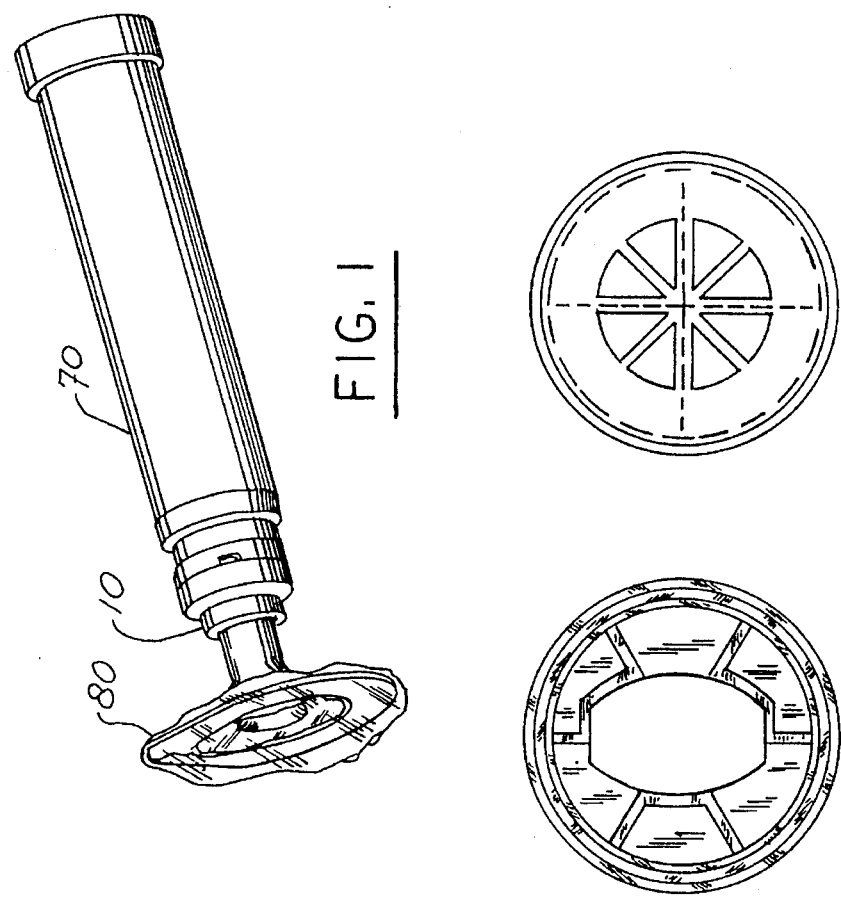

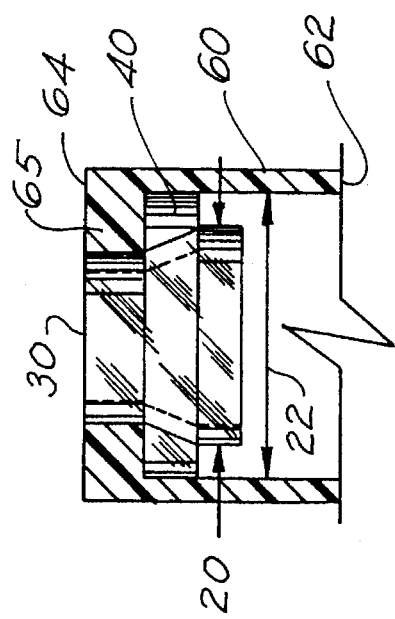
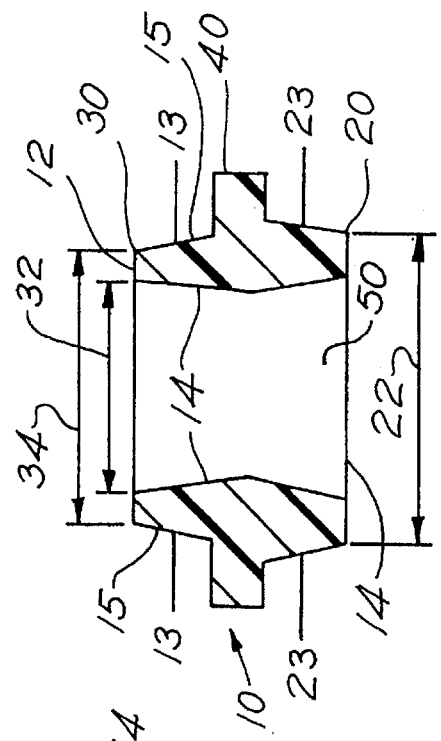
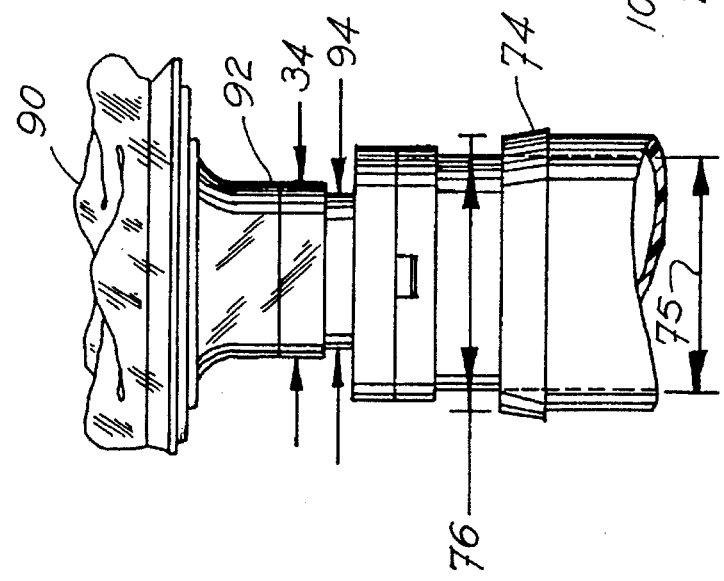
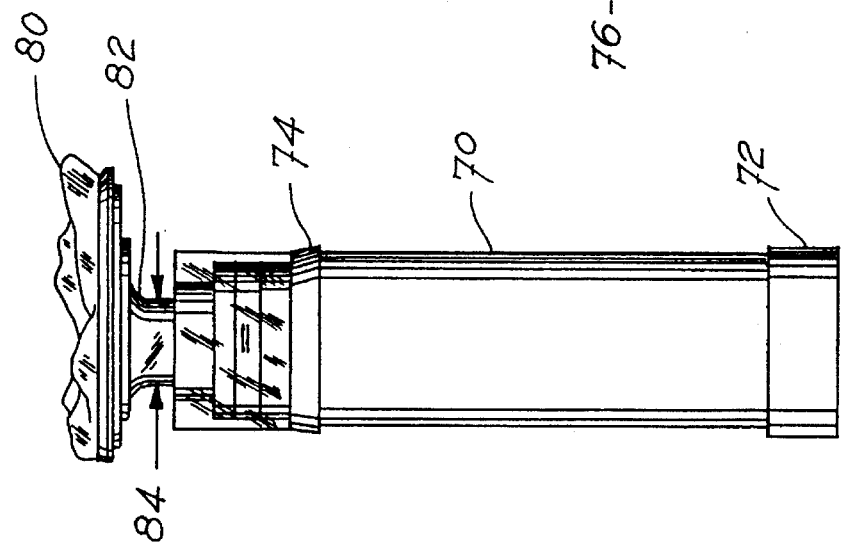

1

NEBULIZER MASK ADAPTOR RING

BACKGROUND OF THE INVENTION

This invention relates generally to the field of medical inhalers, and specifically to inhalers fitted with extended breathing tubes and face masks for children and adults.

It has been found that an extension of the traditional inhaler will result in a better misted inhalant and more effective treatment of asthmatic attacks and other bronchial distress. Further, to ensure proper inhalation, especially in infants, breathing masks have been found to be more effective than traditional inhalers.

For example U.S. Pat. No. 4,470,412 (Nowacki et al.) discloses an extended cylinder attachment to a standard inhaler. U.S. Pat. No. 4,809,692 (Nowacki et al.) and U.S. Pat. No. 4,832,015 (Nowacki et al.) develop that concept further and introduce pediatric masks for attachment to extended breathing cylinders.

Typically, these breathing masks have different sizes of connectors to the inhaler extension depending on the function of the mask, that is whether the mask is for a child or an adult. Because of the different sizes of connectors, a single standard inhaler extension may not be used. Different extensions are required for different masks. U.S. Pat. No. 5,012,803 (Foley et al.) discloses a modular medication inhaler that may be manufactured with several different outlet ends depending on which mask will be attached to the extension.

The present invention is a mask adaptor ring that allows connection of the extended tube outlet to adult- and child-sized masks. The inventor knows of no such device in the prior art.

It is an objective of the present invention to provide a single mask adaptor ring that will allow connection of either a children's or an adult's mask to the extended cylindrical breathing tube.

It is a further objective of the present invention to provide a mask adaptor ring that may be connected to any size outlet in an extended breathing tube.

SUMMARY OF THE INVENTION

The present invention is a mask adaptor ring for use with a modular medication inhaler having an extended breathing tube and with masks having attachment connections with different sizes. The mask adaptor ring is a compound annular ring with a central opening. It has inlet and outlet ends. At its outlet end it has an outside diameter sized to fit into the attachment for an adult size breathing mask. At its outlet end its inside diameter is sized so that the attachment for a child size mask fits inside of it. This allows for multiple uses for the normally single use extended cylindrical breathing tube. The inlet end of the mask adaptor ring is sized so that it will fit standard cylindrical breathing tubes, but may be fitted with a skirting so that it may be attached to any size extended cylindrical breathing tube. The middle part, or center flange, of the compound annular ring has a diameter larger than the outer diameter of the adult breathing mask and of the outlet end opening of the extended cylindrical breathing tube.

DESCRIPTION OF THE DRAWINGS

FIG. 1 is a perspective view of an extended inhaler tube and a mask connected by the mask adaptor ring.

FIG. 2 is an outlet end view of a typical extended inhaler tube.

FIG. 3 is an inlet end view of a typical extended inhaler tube.

FIG. 4 is an exploded front view of the mask adaptor ring and a typical extended inhaler tube and mask.

FIG. 5 is a front view of the mask adaptor ring and skirting as used on a typical extended inhaler tube and mask.

FIG. 6 is a front view of the connection of a typical mask and extended inhaler tube with the mask adaptor ring.

FIG. 7 is front sectional view of the mask adaptor ring and skirting.

FIG. 8 is a front sectional view of the mask adaptor ring.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Referring to FIG. 8, the mask adaptor ring 10 may be seen. The mask adaptor ring 10 is a compound annular ring having an inlet end 20, an outlet end 30, a center flange 40 and a central opening 50. Outlet end 30 is cylindrical in shape, having inside diameter 32 and outside diameter 34. Central opening 50 of mask adaptor ring 10 is tapered at inside diameter 32 of the outlet end 30. Outside diameter 34 of outlet end 30 is also tapered. Inside diameter 32 is at its widest at top 12, and is tapered inward at an angle of 1°–4° so that it is at its narrowest at center flange 40. Outside diameter 34 is at its narrowest at top 12, and is tapered outward at an angle of 1°–4° so that it is at its widest at center flange 40. As may be seen in FIGS. 4 and 8, and also FIG. 5 inside diameter 32 is tapered so that it is slightly wider at top 12 than the outer diameter 84 of mask attachment 82 of the child size mask but that at roughly the midway point 13, between top 12 and center flange 40, the inside diameter 32 narrows slightly so that, the outside diameter 84 of the mask attachment 82 of child mask 80, shown in FIG. 5 will tightly engage the inside surface 14 of the adaptor ring 10. As may be seen in FIG. 6, outside diameter 34 is similarly tapered or sized so that it is slightly narrower at top 12 and wider at center flange 40. Accordingly at the midway point 13 between top 12 and center flange 40, outside diameter 34 is slightly wider than the inner diameter 94 of mask attachment 92 for adult mask 90. Consequently, inner diameter 94 of the adult mask 90 will engage outside surface 15 of outlet end 30 and provide a tight, friction-sealed attachment to the adaptor ring 10. Thus, the adaptor ring 10 works for both child mask 80 and adult mask 90.

Referring to FIGS. 6, 7, and 8, inlet 20 of mask adaptor ring 10 has outer diameter 22 sized so that at midway point 23 outer diameter 22 will fit the standard inner diameter 75 of outlet end 74 of extended cylindrical tube 70. In this manner, it may be quickly and easily used to attach the extended cylindrical tube 70 to children's mask 80 or adult's mask 90. Outer diameter 22 is at its narrowest at bottom 14, and is tapered at an angle of 1°–4° so that it is at its widest at center flange 40.

Central opening 50, outer diameter 22, and outside diameter 34 are tapered to allow for variations in size of mask attachments 82 and 92, and outlet ends 74 of extended cylindrical tubes 70.

Taking into account variance in size of inner diameters 75 of outlet ends 74 of extended cylindrical tubes 70, the invention 10 also may alternatively include a resilient skirt 60, sized at its inlet end 62 to be slightly larger than outside diameter 76 of extended cylindrical tube 70, with outlet end 64 having an inwardly directed flange 65 sized so that outlet opening 66 is slightly larger than outside diameter 34 of outlet end 30 of mask adaptor ring 10. In this manner skirting 60 allows connection of mask adaptor ring 10 to an extended cylindrical tube 70 even if inlet end 20 and tube outlet end 74 do not have substantially the same diameters.

The mask adaptor ring 10 is preferably made of plastic, but may be made of any other suitable material. Preferably the inside diameter 32 and outside diameter 34 of outlet end 30 are sized to fit standard child masks 80 and adult masks 90, and outer diameter 20 is sized to fit standard inner diameters 75 of extended cylindrical tubes, such as those sold under the trademark AEROCHAMBER manufactured by Monaghan Medical Corporation and disclosed in U.S. Pat. Nos. 4,470,412, 4,809,692, 4,832,015, and 5,012,803.

The method of using the mask adaptor ring 10 is as follows. The mask adaptor ring 10 is attached either by itself or with skirting 60 to extended cylindrical tube 70, after which children's mask 80 or adult's mask 90 is attached to mask adaptor ring 10. Following that, the mask is applied to a child's or an adult's face for inhalation of medication.

The above described embodiments of this invention are merely descriptive of its principles and are not to be limited. The scope of this invention instead shall be determined from the scope of the following claims, including their equivalents.

What is claimed is:

1. A method of inhaling medication from a modular medication inhaler through a mask the method comprising the steps of providing a mask adaptor ring comprising a compound annual ring having a bottom with an inlet end, a top with an outlet end, and an opening extending from the inlet end to the outlet end; the outlet end having a tapered outside diameter and a tapered inside diameter; the largest diameter of the tapered inside diameter of the outlet end being slightly larger than the outer diameter of the children size mask attachment means; the smallest diameter of the tapered outside diameter of the outlet end being slightly smaller than the inner diameter of the adult size mask attachment means; the inlet end of the compound annular ring being sized to fit the outlet of the extended cylindrical breathing tube of the modular medication inhaler, attaching the inlet end of the mask adaptor ring to the extended cylindrical breathing tube;

attaching the mask attachment means to the outlet end of the mask adaptor ring;

placing the mask over the nose and mouth of a person receiving the medication; and discharging the medication through the cylindrical breathing tube, the mask adaptor ring, and the mask.

\* \* \* \* \*